United States Patent
Byhmer et al.

(10) Patent No.: US 10,933,185 B2
(45) Date of Patent: Mar. 2, 2021

(54) DEVICE FOR MONITORING HOSE CONNECTORS AND BODY FLUID LEAKAGE

(71) Applicant: REDSENSE MEDICAL AB, Halmstad (SE)

(72) Inventors: Patrik Byhmer, Halmstad (SE); Susanne Olausson, Halmstad (SE)

(73) Assignee: REDSENSE MEDICAL AB, Halmstad (SE)

( * ) Notice: Subject to any disclaimer, the term of this patent is extended or adjusted under 35 U.S.C. 154(b) by 127 days.

(21) Appl. No.: 16/333,571

(22) PCT Filed: Sep. 15, 2017

(86) PCT No.: PCT/SE2017/000037
§ 371 (c)(1),
(2) Date: Mar. 14, 2019

(87) PCT Pub. No.: WO2018/052353
PCT Pub. Date: Mar. 22, 2018

(65) Prior Publication Data
US 2019/0255243 A1 Aug. 22, 2019

(30) Foreign Application Priority Data
Sep. 16, 2016 (SE) .................................. 1630226-7

(51) Int. Cl.
*A61M 1/36* (2006.01)
*A61M 5/168* (2006.01)
(Continued)

(52) U.S. Cl.
CPC ....... *A61M 1/3656* (2014.02); *A61B 5/14557* (2013.01); *A61M 1/36* (2013.01);
(Continued)

(58) Field of Classification Search
CPC .... A61M 1/3656; A61M 1/3653; A61M 1/36; A61M 2205/15; A61M 2205/3306;
(Continued)

(56) References Cited

U.S. PATENT DOCUMENTS 5,230,350 A * 7/1993 Fentress ................ A61F 15/008
128/846
5,301,690 A 4/1994 Lewis et al.
(Continued)

FOREIGN PATENT DOCUMENTS

DE 11 2012 003 387 2/2013
EP 2 604 303 A1 6/2013
(Continued)

OTHER PUBLICATIONS

Extended European Search Report issued in corresponding European Applciation No. 17851174.7 dated Mar. 31, 2020.

*Primary Examiner* — John R Lee
(74) *Attorney, Agent, or Firm* — Birch, Stewart, Kolasch & Birch, LLP

(57) ABSTRACT

A device for monitoring fluid leakage. A flexible plastic sheet (11) is provided with a tear-off strip (12), which divides the sheet in a first sheet portion (21) and a second sheet portion (20) and forms a folding line. An adhesive (22) is arranged at the first portion (21). The sheet is folded along the folding line and the first portion is attached to the second portion via the adhesive to form a pocket along the folding line for enclosing a connector and hose assembly to be monitored. An optical sensor having an absorbent pad and an optical fiber is enclosed in said pocket when formed. The exterior end of the optical fiber is connected to an optical detector device for monitoring if the interior end of the optical fiber comes into contact with a fluid, indicating a leakage of the connector.

21 Claims, 6 Drawing Sheets

(51) Int. Cl.
*G01J 1/04* (2006.01)
*G01J 1/44* (2006.01)
*A61B 5/1455* (2006.01)
*A61B 5/00* (2006.01)

(52) U.S. Cl.
CPC ....... *A61M 5/16831* (2013.01); *G01J 1/0425* (2013.01); *G01J 1/44* (2013.01); *A61B 5/6866* (2013.01); *A61M 2205/15* (2013.01); *A61M 2205/3306* (2013.01)

(58) Field of Classification Search
CPC ........... A61M 5/16831; A61B 5/14557; A61B 5/14551; A61B 5/14552; A61B 5/1455; A61B 5/6866; G01J 1/44; G01J 1/0425
See application file for complete search history.

(56) References Cited

U.S. PATENT DOCUMENTS

| | | | |
|---|---|---|---|
| 5,579,765 A * | 12/1996 | Cox | A61B 5/02042 600/307 |
| 6,445,304 B1 | 9/2002 | Bandeian, Jr. et al. | |
| 6,979,306 B2 * | 12/2005 | Moll | A61B 5/02042 210/646 |
| 7,708,720 B1 * | 5/2010 | Angstrom | A61M 25/02 604/263 |
| 8,048,045 B2 | 11/2011 | Engvall | |
| 8,187,184 B2 | 5/2012 | Muller et al. | |
| 8,696,571 B2 * | 4/2014 | Marttila | A61M 5/158 600/371 |
| 8,808,218 B2 * | 8/2014 | Cazzini | A61M 1/3659 604/6.16 |
| 9,731,086 B2 | 8/2017 | Heppe et al. | |
| 2002/0198483 A1 * | 12/2002 | Wariar | A61B 5/150961 604/5.01 |
| 2005/0038325 A1 | 2/2005 | Moll | |
| 2006/0130591 A1 | 6/2006 | Perkins | |
| 2013/0211329 A1 * | 8/2013 | Kamatani | A61M 5/16831 604/111 |
| 2016/0158517 A1 * | 6/2016 | Nebbia | A61M 5/16836 604/111 |
| 2016/0166438 A1 * | 6/2016 | Rovaniemi | A61F 13/00059 600/301 |
| 2016/0166756 A1 * | 6/2016 | Heppe | A61M 1/3656 604/263 |
| 2016/0325038 A1 | 11/2016 | Schroers | |
| 2019/0255243 A1 * | 8/2019 | Byhmer | G01M 3/38 |

FOREIGN PATENT DOCUMENTS

| | | |
|---|---|---|
| KR | 10-2007-0043692 A | 4/2007 |
| WO | WO 99/24145 A1 | 5/1999 |
| WO | WO 2006/001759 A1 | 1/2006 |
| WO | WO 2006/008866 A1 | 1/2006 |
| WO | WO 2013/025815 A1 | 2/2013 |
| WO | WO 2013/147670 A1 | 10/2013 |

* cited by examiner

DEVICE FOR MONITORING HOSE CONNECTORS AND BODY FLUID LEAKAGE

FIELD OF INVENTION

The present invention relates to a device for monitoring the patency of hose connectors and for detecting leakages of fluid out of the hoses or connectors, specifically in the medical area.

BACKGROUND OF THE INVENTION

WO2006/001759A1 discloses a method and means for detection of blood leakage from wounds by means of an optical fiber. The optical fiber is arranged in a loop from a light source to a patch to be attached to the patient and back to a light detector. The light source and light detector are arranged in a monitoring device at a distance from the patch and may be attached to the arm of a patient. The loop comprises a sensor portion arranged at the patch and in which the optical fiber is bent with a small radius, so that the total internal reflection angle inside the optical fiber is approached or exceeded. A portion of the light transmitted through the optical fiber passes out through the sidewall of the optical fiber in the small radius sensor portion. When the sensor portion is exposed to a fluid, such as water or blood, the portion of the light passing out through the sidewall of the optical fiber in the small radius sensor portion increases, which may be sensed by the light detector as a decrease in light intensity, which may trigger an alarm.

WO2013/147670A1 discloses a device for monitoring a skin surface for leakage of blood at, for example, a wound or a vascular access. The device comprises a patient unit, a connection unit and a monitor unit. The patient unit comprises a patch, including an adhesive layer to be attached to the skin surface of the patient. The adhesive layer is arranged to attach the patch to the skin so that a predetermined removal force, such as 30 N, is required for removing the patch from the skin surface. A patient optical fiber is arranged at the patch and has a proximal end for connection to the connection unit. A patient connector is arranged at the distal end of a connection optical fiber. The connector has an opening passing through the connector, whereby the connection optical fiber is arranged in one end of the opening. The patient optical fiber may be inserted in the other end of the opening so that the proximal end of the patient optical fiber is arranged in register with the distal end of the connection optical fiber in order to transmit light between the optical fibers. A spring is arranged in the connector for exerting a force at the patient optical fiber at a side surface thereof for preventing unintentional withdrawal of the patient optical fiber. However, when the withdrawal force is larger than the removal force of the patch, the patient optical fiber is withdrawn from the connector. Thus, the patch is not removed from the skin even when a large force is exerted on the optical fibers.

These previously known devices are designed for monitoring a wound or a vascular access at the skin of a patient, which is a safety risk in an extracorporeal blood circuit. Particularly, a dislocation of a venous needle transporting blood back to the patient from a dialysis machine is a potentially life threatening condition, which may result in the death of the patient if undetected for a few minutes.

Hose connectors are another safety risk in extracorporeal circuits, for example of the type Lure connectors. Such Luer connectors are for example used for connecting the blood hoses to an external dialysis machine or for connecting the blood hose to a venous needle. If a connector fails in an extracorporeal circuit from a dialysis machine and back to a patient venous needle, the situation may be as adverse as described in the above-mentioned prior art devices when a venous needle is accidently removed.

WO 2014/008980A1 discloses a device for detecting moisture for a device or for monitoring an access to a patient for a device with which a liquid is supplied to a patient via a hose line and/or with which a liquid is discharged from the patient, in particular for monitoring the access to a vessel in an extracorporeal blood treatment process, in particular for monitoring a central venous catheter for an acute dialysis. The device comprises one portion which can be deformed into a sleeve and which can be positioned about the circumference of the hose line or a connection system of the hose line. The sleeve-shaped portion has fixing means for fixing the sleeve-shaped portion in the position surrounding the hose line or the connection system. The portion designed in the form of a sleeve allows the device for detecting moisture to be fixed to a hose line or a connection system of the line in a quick and reliable manner.

WO 2015/1214 discloses a cover device for covering a hose system that can be connected to a patient and has a flat structure with a liquid sensor. The liquid sensor is arranged within a convolution of the flat structure in such a way that leaks on the connectors of the hose system can be detected by said liquid sensor, even if the hose system is concealed by the cover device.

However, the sleeve and the structure according to the two above mentioned documents are open in the direction of the hoses, which means that any leakage along the hoses may remain undetected.

An object of the present invention is to provide a safety monitoring device for monitoring the patency of a hose connector wherein a fluid, such as blood, is transported or present inside the hoses and the connector. The connector may be between two hoses or between a hose and a syringe or needle.

SUMMARY OF THE INVENTION

Accordingly, an object of the present invention is to mitigate, alleviate or eliminate one or more of the above-identified deficiencies and disadvantages singly or in any combination.

According to an aspect of the invention, there is provided a device for monitoring fluid leakage in a circuit enclosing said fluid, wherein the circuit comprises hoses and a connector. The device comprises a first sheet of a flexible material; a second sheet of a flexible material; an adhesive layer arranged at said first sheet or said second sheet or both in a pattern for forming a closed pocket when the first sheet and the second sheet are brought together; said closed pocket having a first end and a second end constructed for receiving said hoses and an enlargement area there between constructed for receiving said connector; a detector device arranged for detecting leakage of a fluid into the closed pocket; a tear-off strip, defined by weakening lines extending from said first end to said second end of said pocket; whereby the first portion is attached to the second portion via said adhesive layer to form said closed pocket for enclosing said hoses and connector to be monitored.

In an embodiment, the tear-off strip may be formed by two weakening lines arranged in parallel with a mutual distance across said first or second sheet. The first sheet may be connected to said tear-off strip by a first weakening line and said second sheet may be connected to said tear-off strip by a second weakening line, whereby the first sheet, the tear-off strip and the second sheet form a single flexible sheet. The adhesive may be arranged with a distance to said tear-off strip.

In another embodiment, the closed pocket may be formed between the first sheet and the second sheet, and at least one of the first or second sheet is free from an adhesive layer in an area forming the closed pocket.

In a further embodiment, the detector device may be an optical sensor arranged at the first or second sheet in a position to be included in the closed pocket when formed.

In a still further embodiment, an indentation free from adhesive is formed in the adhesive portion for forming the enlargement area.

In another aspect, the device as mentioned above may further comprise a connector assembly is arranged along said tear-off strip for being enclosed in said pocket. A fixation device may be arranged for fixation of the connector assembly.

In a yet further embodiment, the optical sensor may comprises: an absorbent pad arranged at the middle of said tear-off strip or adjacent the middle of said tear-off strip and at said first portion comprising said adhesive; and an optical fiber, having an internal end arranged in said absorbent pad and en external end extending out of the sheet.

BRIEF DESCRIPTION OF THE DRAWINGS

Further objects, features and advantages of the invention will become apparent from the following detailed description of embodiments of the invention with reference to the drawings, in which.

DETAILED DESCRIPTION OF EMBODIMENTS

Figure 1:
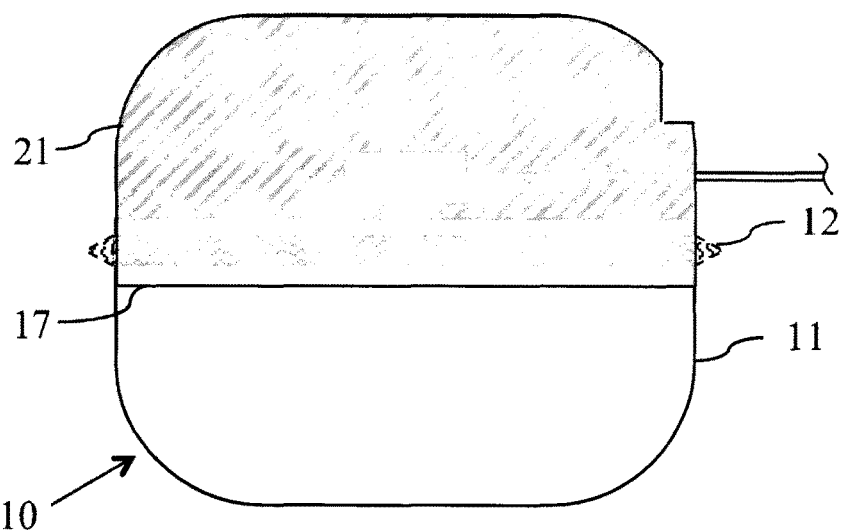
FIG. 1 is a plan view of a first embodiment of a connector monitoring device according to the invention.

Below, several embodiments of the invention will be described. These embodiments are described in illustrating purpose in order to enable a skilled person to carry out the invention and to disclose the best mode. However, such embodiments do not limit the scope of the invention. Moreover, certain combinations of features are shown and discussed. However, other combinations of the different features are possible within the scope of the invention.

In an extracorporeal blood circuit, wherein blood is removed from the living body and transported to a treatment machine, such as a dialyzing machine, there is always a risk of malfunctioning. If the blood circuit is compromised in any manner, there is a risk that blood will be removed from the body but not properly returned to the body. Such a condition will result in that the blood volume in the body will decrease and if such a decrease is rapid and large, the situation is life threatening.

An extracorporeal circuit comprises several weak points, where there is a likelihood of malfunctioning or hazard risk. Such weak point are connectors between hoses in the circuit or between a hose and a needle. The extracorporeal circuit may comprise a body fluid, which may be blood.

A similar problem exists in other circuits comprising liquids other than body fluids, for example infusion fluids comprising pharmaceuticals, wherein a leakage in a connector may be hazardous.

Other circuits that may be monitored are closed circuits comprising strong acids or strong bases, or other fluids that are harmful if they escape the closed circuit.

The present invention provides a solution to such problems by means of a device for monitoring such connectors and detecting leakage of a fluid or liquid.

There are multiple reasons for leakage of a connector. The connector may be exposed to lateral or bending forces, which temporarily or permanently opens a flow path out of the connector. If the connector is exposed to excessive forces, a leakage may result. The connector may comprise weak points during manufacture, which break at certain conditions. The hose being connected to the connector may be erroneously arranged so that a leakage exists. The connectors may be exposed to solvents or sterilizing agents that may cause a leakage. If the plastics material is exposed to light, particularly ultra-violet light, the material may decompose finally causing a leakage. There are multiple other causes of a leakage.

The most common cause of malfunctioning is probably tear and wear, which finally results in a break or a leakage. The leakage may be small but continuous so that a prolonged use results in a hazard. However, in several cases, such leakage starts at a certain time instant and is large, whereby a hazardous condition rapidly develops.

The basis idea of the present invention is to provide a monitoring device in the nature of a closed pocket surrounding the connector and parts of the connected hoses. If the pocket is closed, any fluid leaking out into the pocket is confined to the interior of such a pocket whereby the leakage may be decreased or even stopped. The closed pocket should have a small size, smaller than 20 ml or smaller than 10 ml.

In addition, a fluid detector is arranged inside the closed pocket. The fluid detector should be of a non-electric type, since electricity should be avoided in the vicinity of blood.

An optical type detector may be used, for example a detector as disclosed in WO2013/147670A1. Another type of non-electric detector may be a RFID tag embedded in an absorbent pad. If the pad receives moisture, the RFID tag can no longer be detected by an interrogator, see U.S. Pat. No. 7,755,488B2. A magnetic detector may alternatively be used.

The arrangement of a closed pocket surrounding the connector may also results in a reinforcement or stabilization of the connector, whereby the connector may resist bending forces.

The pocket may be formed after the assembly of the extracorporeal circuit.

The pocket is constructed of flexible sheet or film provided with adhesive over at least a portion of its surface. The film is folded or otherwise arranged around the connector and adjacent hoses and the adhesive sticks to the film at both sides of the connector, whereby a closed pocket is formed.

The closed pocket does not need to be closed in an airtight manner. However, a closed pocket in the sense of this specification means a pocket, which confines any leakage from the connector to the closed pocket and wherein any possible leakage out of the pocket is less than 0.1 ml/min or less than 0.01 ml/min.

The monitoring device should be able to be removed from the hose and connector assembly with minimal influence upon the hose and connector assembly. For example, if the closed pocket is arranged at a connector connecting a venous needle with a blood hose, the monitoring device should be able to be removed without disturbing the venous needle operation. If the adhesive sticks to the hose and connector assembly, it will be difficult to remove the monitoring device. Thus, the closed pocket is formed so that the adhesive sticks to the hose and connector only to a small extent, as will be explained below. In addition, a tear-off strip is arranged, as will be explained below.

FIG. 1 shows a first embodiment of a monitor device for a connector assembly. The monitor device 10 comprises a plastic sheet 11 having a rectangular or oval shape. A tear-off strip 12 is formed by two weakening lines 13 and 14 arranged in the plastic sheet approximately in the middle thereof, forming two interconnected portions of the plastic sheet, an upper sheet portion 21 and a lower sheet portion 20. The two portions may be substantially equally large. A triangular grip portion 15, 16 may be arranged at one or both ends of the tear-off strip 12. The tear-off strip may have a different color compared to the rest of the plastic sheet 11, such as red. The tear-off strip may be reinforced, for example by additional material connected to the tear-off strip portion. The tear-off strip may be arranged at a portion of the plastic sheet which does not comprise an adhesive, see further below.

Figure 5:
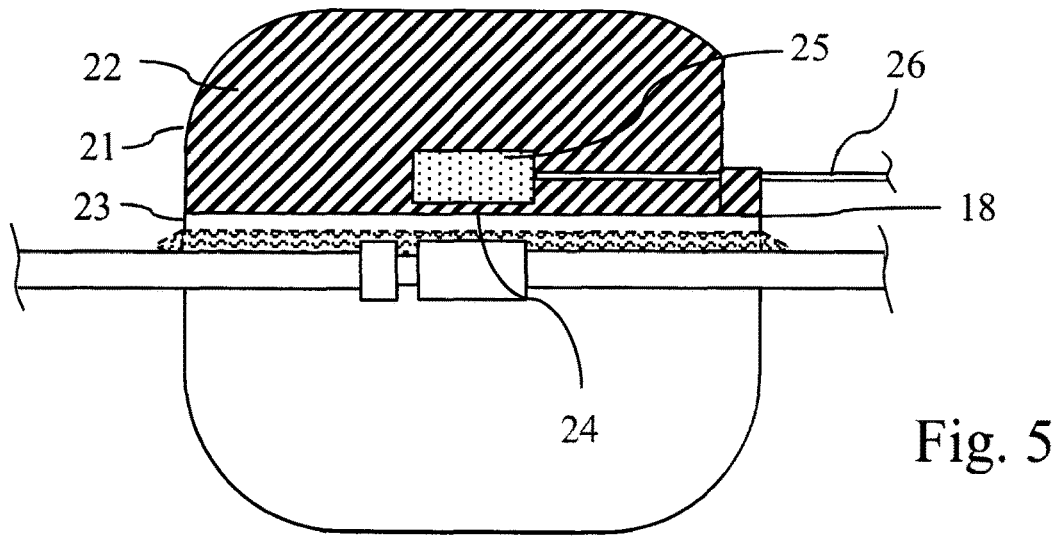
FIG. 5 is a plan view of the first embodiment in a fourth step of mounting.

The upper portion 21 of the plastic film 11 is provided with an adhesive 22, as is more clearly visible in FIG. 5. The lower portion 20 of the plastic film does not comprise an adhesive. The adhesive portion is covered by a removable protection sheet 17.

The expressions "upper portion" and "lower portion" define the portions as seen in the drawings, in particular FIG. 1 and FIG. 5. "Upper" and "lower" do not define the arrangement of the monitoring device in relation to the hose and connector assembly. The monitoring device may be oriented in any direction suitable for facilitating the mounting and assembly of the monitoring device.

The adhesive is arranged over substantially the entire surface of the upper portion 21, except for a portion adjacent the tear-off strip, as shown. There is a first distance 23 (see FIG. 5) between the adhesive and the tear-off strip, as will be explained below.

An absorbent pad 25 is arranged at the adhesive portion, substantially in the middle and at a second distance 24 from the tear-off strip which is slightly larger than said first distance. An optical fiber 26 is inserted in the absorbent pad and extends substantially parallel with the tear-off strip 12 and extends a certain distance out of the rectangular sheet, for example about 10 cm or further, for example about 30 cm.

The exterior end of the optical fiber 26 may be connected to a detector device of any type, for example the detector device disclosed in the above-mentioned WO2013/147670A1, the technical contents of which is incorporated in the present specification by reference. The detector device comprises a light source and a light detector and electric circuitry for determining when a fluid is present at the interior end of the optical fiber inserted in the absorbent pad. Such detection may be arranged by cutting the interior end of the optical fiber at an angle or shaping the interior end so that total internal reflection angle is not exceeded, whereby all light passing into the fiber is reflected back when the interior end is surrounded by air. When the interior end of the optical fiber is covered with a liquid, almost no light is reflected, which may be detected. The detection may also be based on absorbency of blood, which absorbs green light more than red light.

The optical fiber may be fixed to the sheet by folding a tab 18 around the fiber as shown in FIG. 5.

Figure 2:
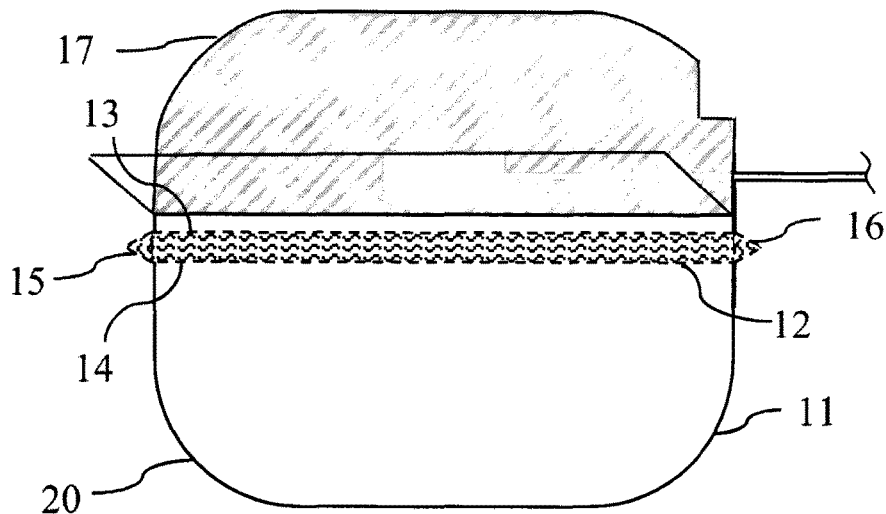
FIG. 2 is a plan view of the first embodiment in a first step of mounting.

The protection sheet 17 extends over the upper portion 21, which comprises adhesive and further down beyond the tear-off strip 12 and into the lower portion 20, as shown in FIG. 1. The lower portion of the protection sheet may be freely folded up as shown in FIG. 2, because there is no adhesive below the protection sheet in this area.

The monitor is arranged on a Luer connector assembly as shown in FIGS. 3 to 7. A connector assembly 31 comprises a male type Luer connector 32 attached to a left hose 33 and a female type Luer connector 34 attached to a right hose 35. The male and female Luer connectors are connected to each other before the arrangement of the monitor device.

Figure 3:
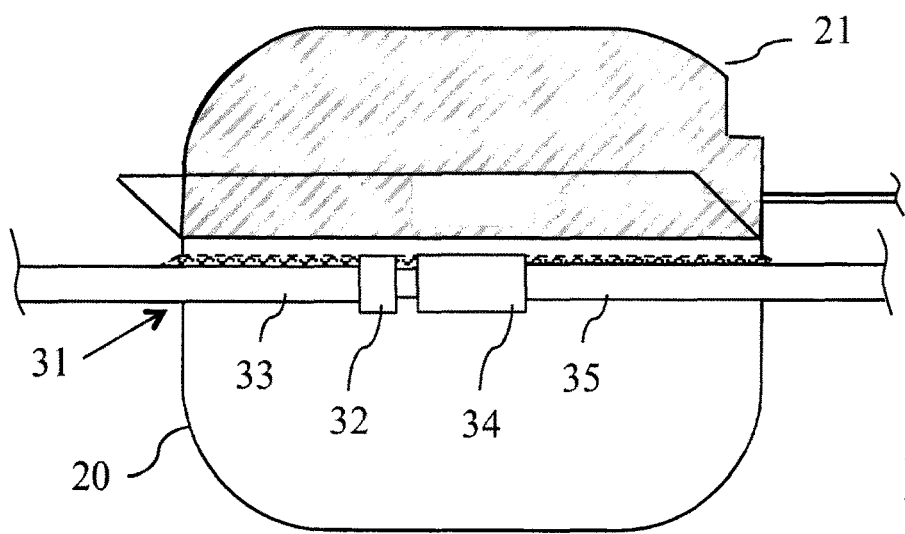
FIG. 3 is a plan view of the first embodiment in a second step of mounting.

As shown in FIG. 3, the connector assembly 31 is arranged at the non-adhesive portion 20 of the monitor 10 substantially in alignment with and parallel with the tear-off strip 12. The lower portion of the protection sheet 17 is folded up. The connector 31 is arranged so that substantially half of the tear-off strip is visible, as shown in FIG. 4.

Figure 6:
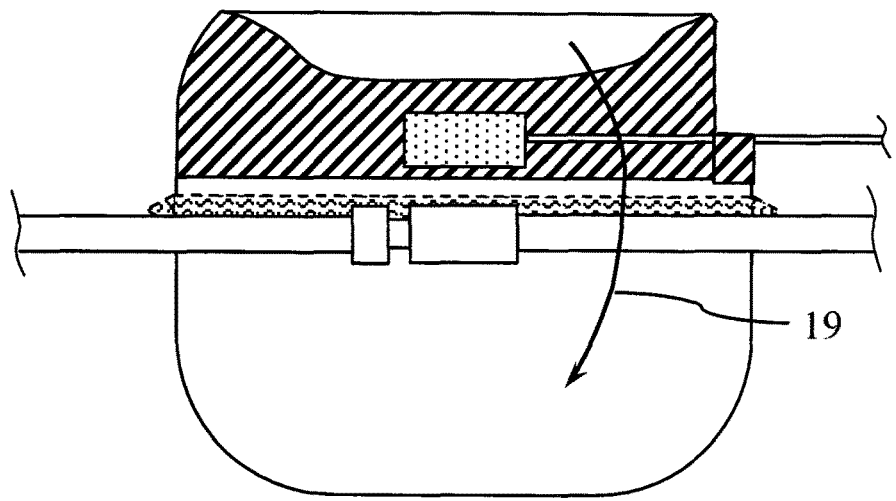
FIG. 6 is a plan view of the first embodiment in a fifth step of mounting.

The protection sheet 17 is removed and the adhesive portion 21 is folded down above the connector 31 as shown by arrow 19 in FIG. 6. By this action, the adsorbent pad 25 will be arranged directly above the Luer connector in the area wherein a leakage may take place. In addition, the adhesive will stick to the non-adhesive surface of the lower portion 20 and a closed pocket will be formed along the folding line between the upper portion 21 and the lower portion 20 along the connector 31 and hoses 33 and 35.

Figure 4:
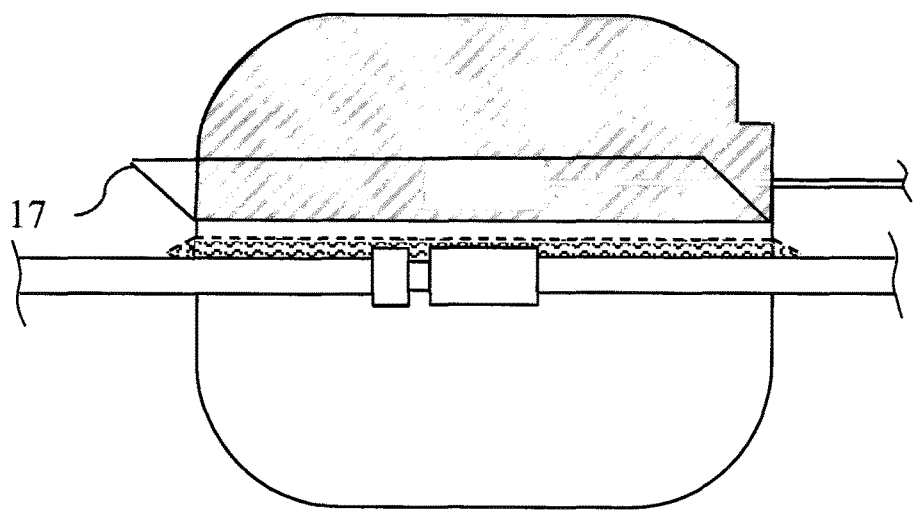
FIG. 4 is a plan view of the first embodiment in a third step of mounting.
Figure 7:
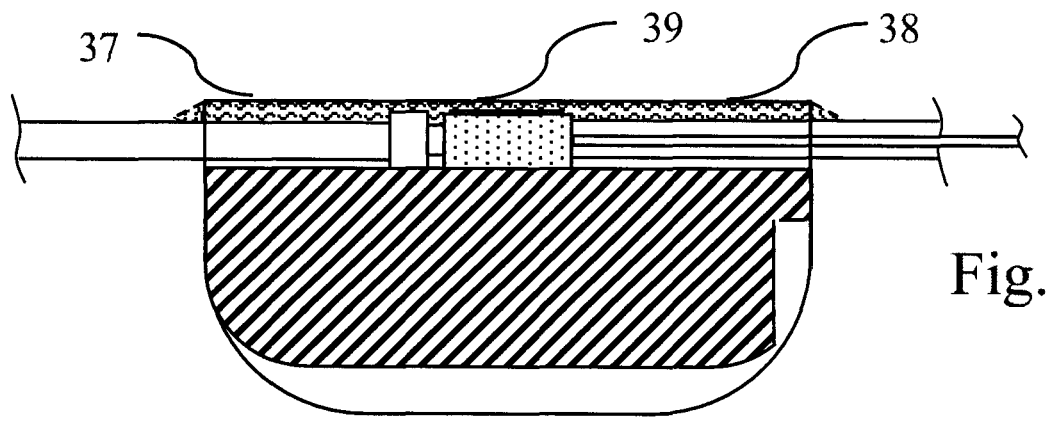
FIG. 7 is a plan view of the first embodiment in a sixth and final step of mounting.

A distance between the connector when arranged as shown in FIG. 4 and the lower part of the adhesive is dimensioned so that the adhesive will not stick to the surface of the hoses but will stick to the non-adhesive lower portion 20 slightly beyond the connector, as shown in FIG. 7.

A closed pocket is formed with a first end 37 to the left in FIG. 7 encircling the left hose 33 and a second end 38 to the right in FIG. 7 encircling the right hose 35 and an enlargement area 39 formed there between encircling the male and female Luer connectors 32, 34. The enlargement area 39 is formed since the Luer connector takes up more space than the left and right hose 33, 35, which means that the plastic sheet forms itself around the Luer connector or bulges out in an enlargement area 39, which is not very visible in FIG. 7.

The adhesive portion 21 may be transparent, so that the proper arrangement of the absorbent pad 25 adjacent the Luer connector may be inspected. The non-adhesive portion 20 may be non-transparent and white so that a leakage of blood may be visual from the outside. The non-adhesive portion 20 may be thicker than the adhesive portion 21, for example having the double or triple thickness. This will make the non-adhesive portion stiffer and more easy to adjust.

Alternatively, the non-adhesive portion 20 is transparent, additionally or separately. In the arrangement described above, the absorbent pad 25 will be arranged at the upper side of the connector 31. This may be reversed by pivoting the whole assembly over 180 degrees after mounting.

When the treatment is finalized and the monitor should be removed, the tear-off strip 12 is ripped off. Such removal of the tear-off strip effectively opens the closed pocket. Thus, the connector and hoses may be removed from the pocket. By the arrangement of said first distance, the adhesive will not stick to the hoses and Luer connectors, or will stick to only a small portion of the hoses or connector.

The closed pocket formed is sealed in relation to the surrounding atmosphere. The pocket should have a small volume of less than about 20 ml or less than 10 ml. Such a small loss of blood is normally not dangerous. The pocket is sealed in relation to the surrounding atmosphere so that less than 0.1 ml/min or less than 0.01 ml/min of liquid may escape to the atmosphere.

If the entire pocket is filled with blood, the absorbent pad and the interior end of the optical fiber will be covered with fluid, which is detected. Also a smaller amount of blood will be absorbed by the absorbent pad and interact with the interior end of the optical fiber and be detected.

Figure 8:
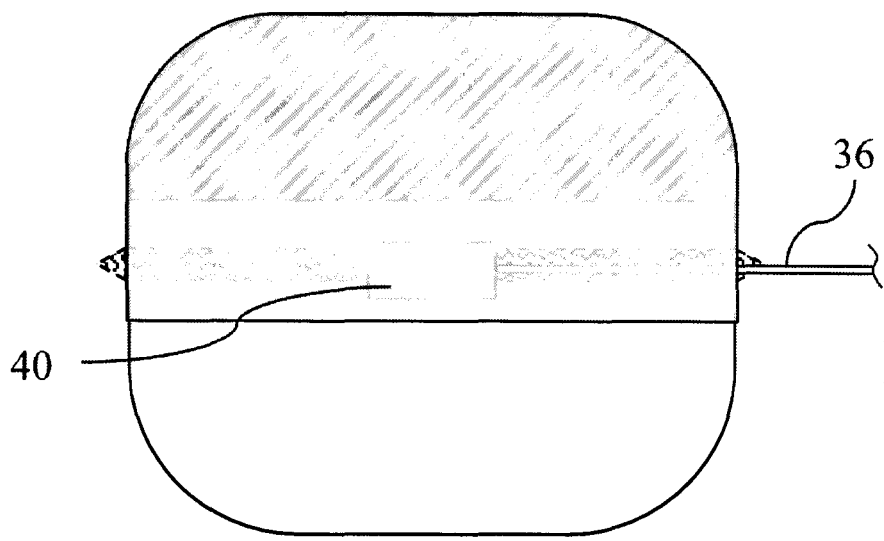
FIG. 8 is a plan view of a second embodiment of a connector monitoring device according to the invention.

A second embodiment is shown in FIG. 8. In the second embodiment the absorbent pad 40 is arranged adjacent the tear-off strip and the optical fiber 36 extends along the tear-off strip. When a connector assembly 31 is arranged at the monitor, the absorbent pad 35 will be positioned below the Luer connector, and possibly in a better position for detecting small leakages. However, the position of the Luer connector may vary as the patient moves.

Figure 9:
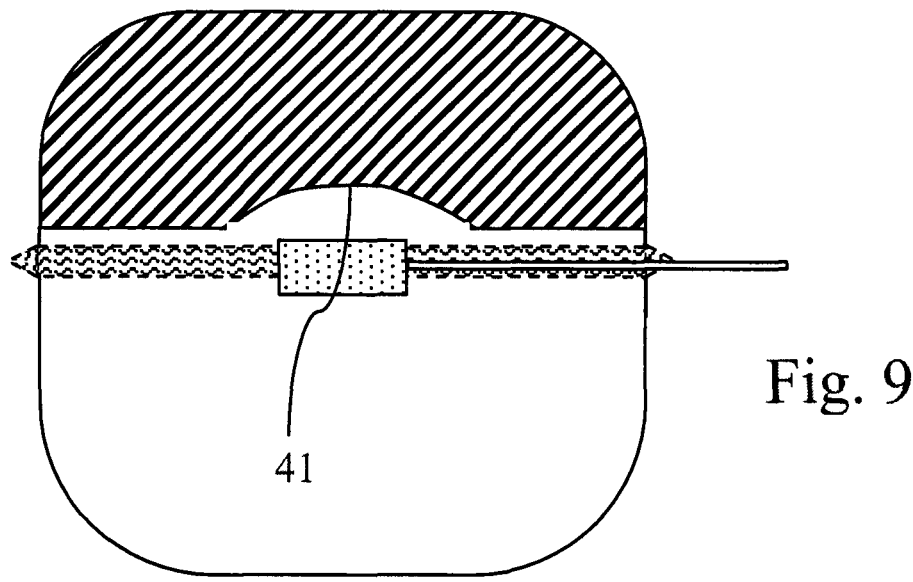
FIG. 9 is a plan view of a third embodiment of a connector monitoring device according to the invention.

FIG. 9 shows a third embodiment of the monitor. The adhesive forms a larger distance to the tear-off strip at the middle by means of an indentation 41. The absorbent pad may be arranged as shown in FIG. 1 or as shown in FIG. 8. By the arrangement of the indentation 41, which is free from adhesive, the adhesive will not stick to the Luer connector when the closed pocket is formed, or at least stick to the Luer connector to a small degree. By this feature, it is more easy to remove the monitor assembly after removal of the tear-off strip 12, since the adhesive sticks to only a small portion of the connector assembly.

Figure 10:
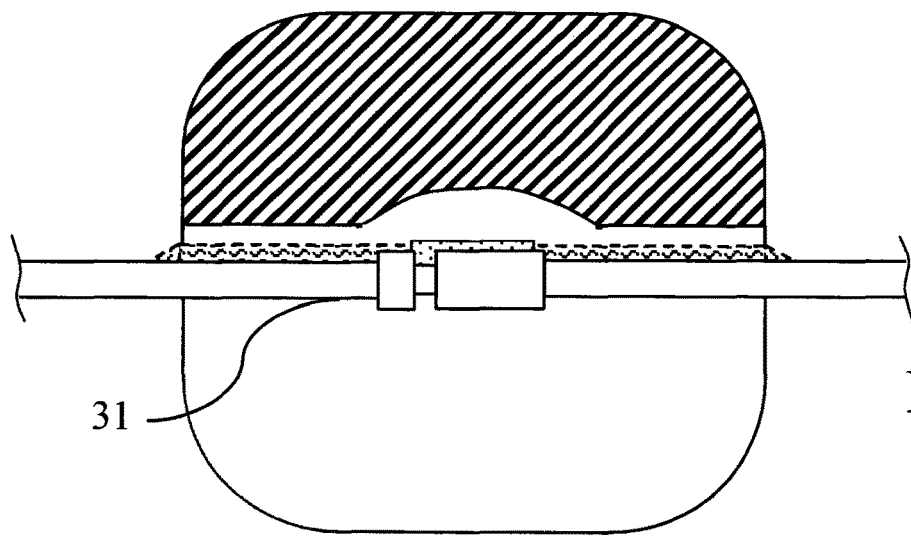
FIG. 10 is a plan view of the third embodiment in a first step of mounting.

FIG. 10 shows the arrangement of the connector assembly 31 so that a portion of the tear-off strip is visible above the connector assembly. When the adhesive portion is folded down as shown in FIGS. 6 and 7, a pocket is formed which is larger at the Luer connector portions in the enlargement area 39 and smaller or non-existent along the adjacent hoses at the first end 37 and second end 38 of the closed pocket.

Figure 11:
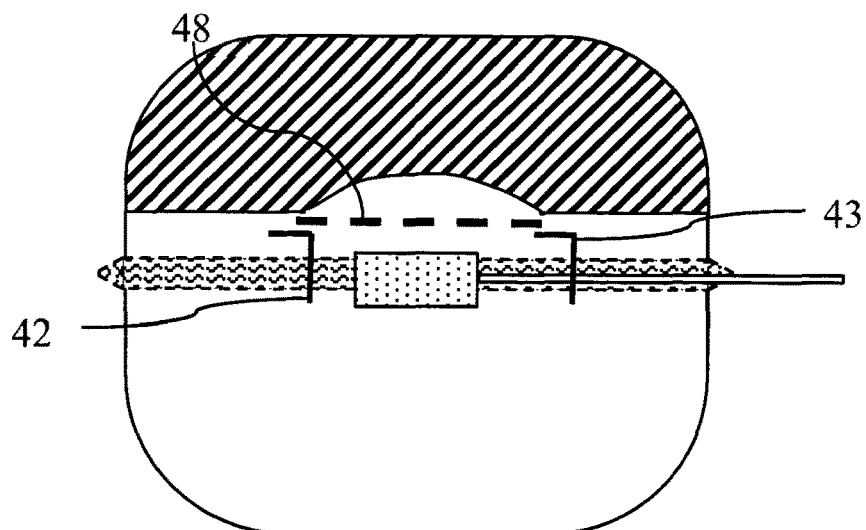
FIG. 11 is a plan view of a fourth embodiment of a connector monitoring device according to the invention.

FIG. 11 shows a fourth embodiment of the invention. Two hook members 42, 43 are arranged and folded down parallel with the monitor sheet. The hooks are made of a stiff material, such as metal. The hook members may be erected for providing a support or holder for the connector assembly, so that the connector assembly is arranged in a correct position before the adhesive portion is folded down.

The fourth embodiment may additionally comprise a reinforcement 48 arranged between the hook members 42, 43 and shown by broken lines in FIG. 11. Said reinforcement may be made of a stiff material such as metal or plastic rib. The reinforcement rib 48 prevents bending forces from bending the Luer connector. Such bending forces may result in leakages. In addition or alternatively, the tear-off strip may be made in a stiff plastic material forming a reinforcement.

The plastic sheet 11 may have different stiffness at the lower portion 20 and the upper portion 21, for example being stiffer at the lower portion. The lower portion may the thicker than the upper portion, for example two or three times thicker. In this manner an additional reinforcement is formed.

Figure 12:
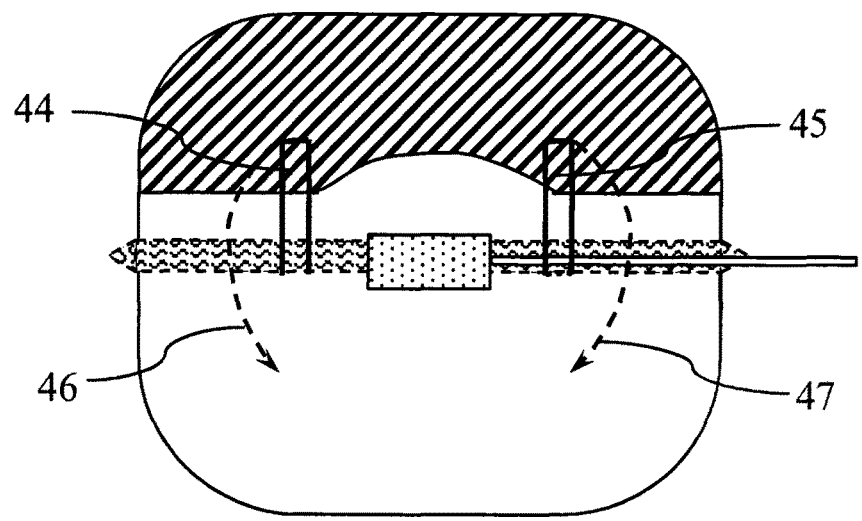
FIG. 12 is a plan view of a fifth embodiment of a connector monitoring device according to the invention.

FIG. 12 shows a fifth embodiment comprising two plastic tabs 44, 45 provided with adhesive. The tabs may be folded down as shown by arrows 46, 47 for immobilizing a connector assembly 31 in a correct position before folding down the adhesive sheet portion 21. In this manner, the adhesive sheet portion may be arranged in a better position since the connector assembly is already provisionally positioned in place.

The plastic sheet is shown to have a rectangular-oval shape, but the sheet may be more oval or triangular or having any desired shape. The plastic sheet may be flexible but non-elastic. Alternatively, the plastic sheet may additionally be elastic.

The lower sheet portion 20 may be slightly larger than the upper portion 21 which comprises the adhesive. Thus, the upper portion will not extend outside the lower portion at the formation of the closed pocket, since the upper portion is slightly smaller.

Figure 13:
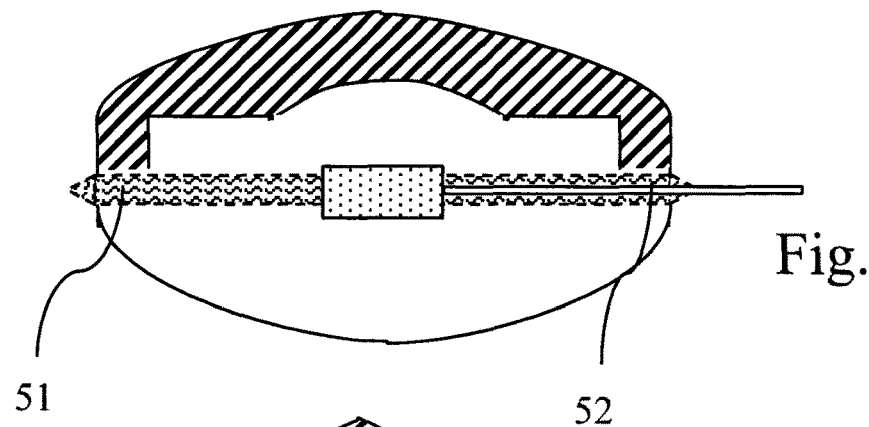
FIG. 13 is a plan view of a sixth embodiment of a connector monitoring device according to the invention.

FIG. 13 discloses an sixth embodiment, in which the adhesive material extends closer to the tear-off strip at both sides of the Luer connector as shown in left tab area 51 and right tab area 52. In this manner, the closed pocket formed may be more securely closed at the first end 37 and second end 38 of the closed pocket. In this manner, no blood or liquid may flow along the hoses and escape the closed pocket undetected. Simultaneously, the central portion of the hoses and the Luer connector itself do not stick to the adhesive because of the enlargement area 39, which is free from adhesive, which means that the monitor device is easily removed by removing the tear-off strip, which effectively opens the closed pocket and the monitor device is easily separated from the Luer connector and hoses without compromising the continued operation of these connectors. In addition, the general shape of the sixth embodiment is oval.

Figure 14:
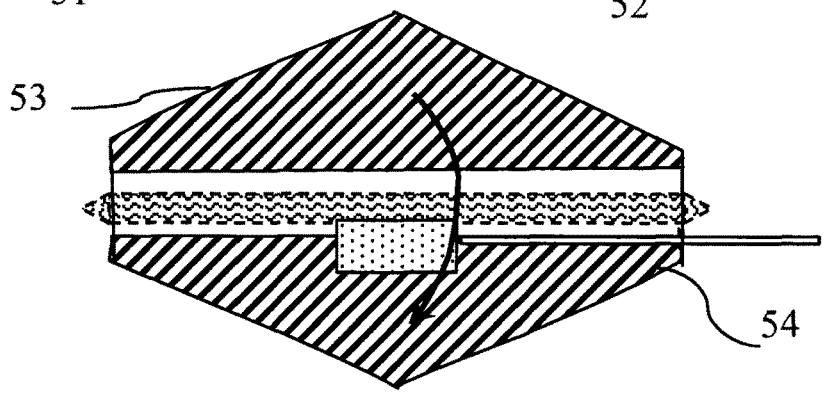
FIG. 14 is a plan view of a seventh embodiment of a connector monitoring device according to the invention.

FIG. 14 discloses a seventh embodiment, which has a generally double triangular shape. In this embodiment, both the upper portion 53 and the lower portion 54 are provided with adhesive. The Luer connector and hoses are first arranged in position along and above the tear-off strip, whereupon the protective sheet (not shown) is removed in order to expose the adhesive. Finally, the upper portion 53 is folded over the Luer connector and hoses and is allowed to stick to the adhesive at the lower portion 54. In this manner, the closed pocket may be arranged so that no glue or only a small amount of glue sticks to the hoses and Luer connector.

The entire surface of the sheet may comprise adhesive, wherein the adhesive is arranged so that it does not stick firmly to the material of the hoses and connectors, but stick together when two surfaces having adhesive are facing and contacting each other. The adhesive may be of a contact type, so that it is not activated until it comes into contact with a surface provided with the same adhesive.

Figure 15:
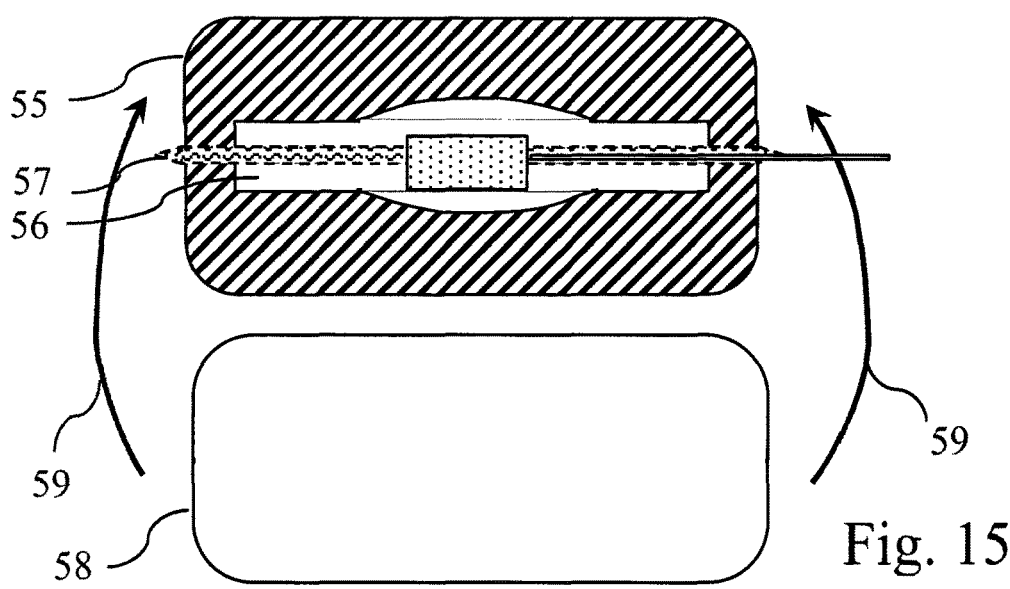
FIG. 15 is a plan view of a eight embodiment of a connector monitoring device according to the invention.

The monitor device may be arranged in two portions as shown in FIG. 15. A first lower portion 55 is arranged below the Luer connector and hose assembly (see FIG. 16). The lower portion 55 is covered by an adhesive except in an area corresponding to the outline of a closed pocket to be formed. Thus, the lower portion 55 comprises a central area 56 which is free from adhesive. The central area is shaped in relation to the connector assembly that should be monitored. A tear-off strip 57 extends over the central area 56.

Figure 16:
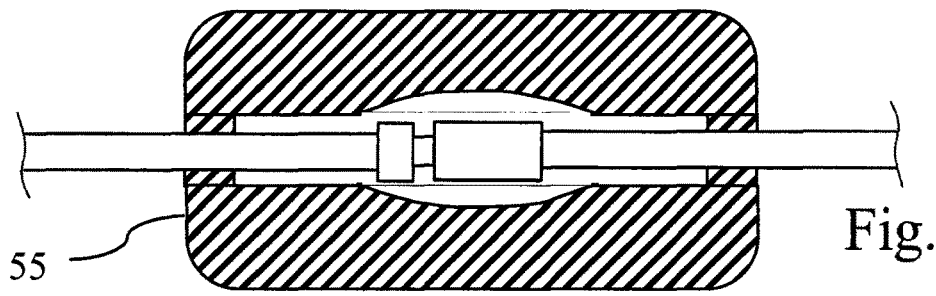
FIG. 16 is a plan view of the eight embodiment of a connector monitoring device according to the invention with a Luer connector in place.

A second separate upper portion 58 is then arranged above the lower portion 55 and Luer connector forming a closed pocket a shown by arrows 59. The lower portion may be stiffer than the upper portion, such as two or three times thicker. FIG. 16 shows the arrangement of the Luer connector assembly at the lower portion 55.

Figure 17:
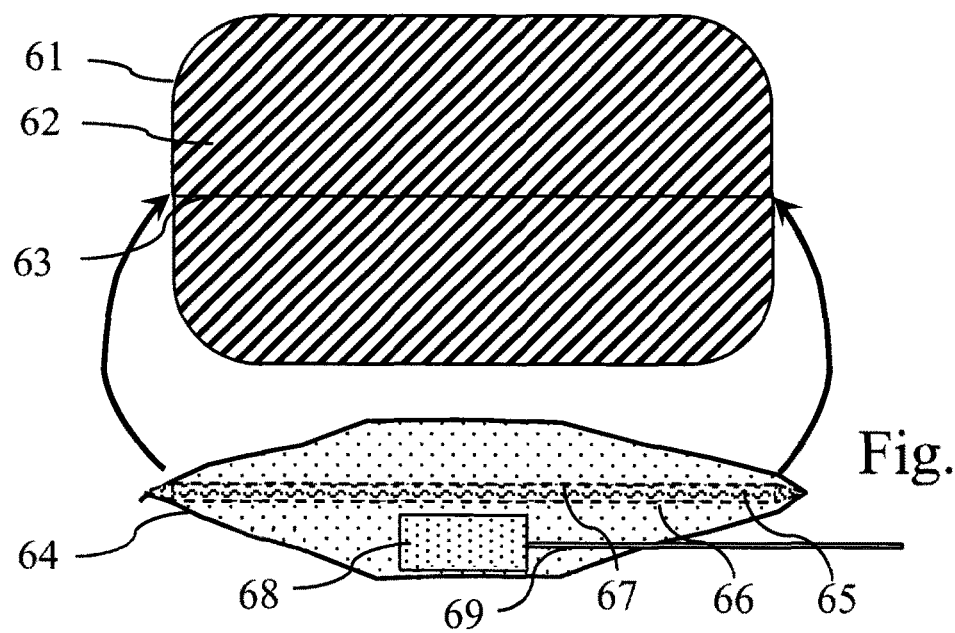
FIG. 17 is a plan view of a ninth embodiment of a connector monitoring device according to the invention in an initial state.

FIG. 17 shows a ninth embodiment of the invention. A lower portion 61 is entirely covered by an adhesive layer 62. A weakening line 63 is formed centrally across the lower portion 61. The lower portion 61 is covered by a protection sheet (not shown) before use.

Figure 19:
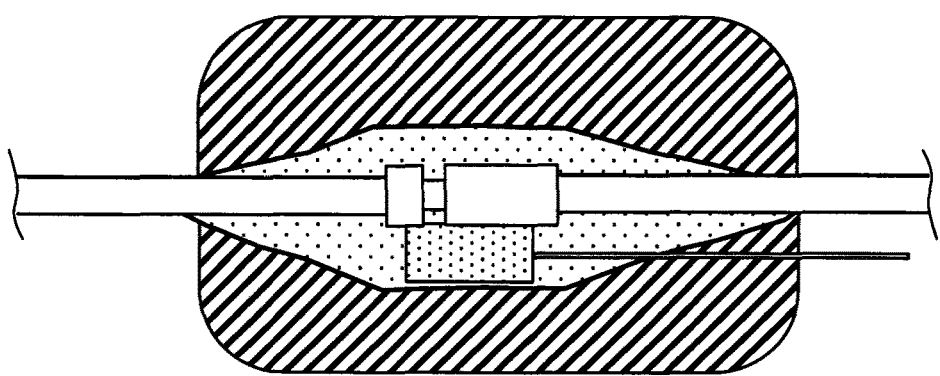
FIG. 19 is a plan view of the ninth embodiment in a third step of mounting.

A separate upper portion 64 is shaped according to the closed pocket to be formed. A tear-off strip 65 is arranged between two weakening lines 66, 67. The upper portion 64 has a large transversal dimension in the middle where the Luer connector should be placed and a smaller transversal dimension at the side where the hoses should be placed (see FIG. 19). The upper portion is provided with an absorbent pad 68 and an optical fiber 69 close to the middle of the upper portion, where the Luer connector should be placed. The upper portion is free from adhesive.

Figure 18:
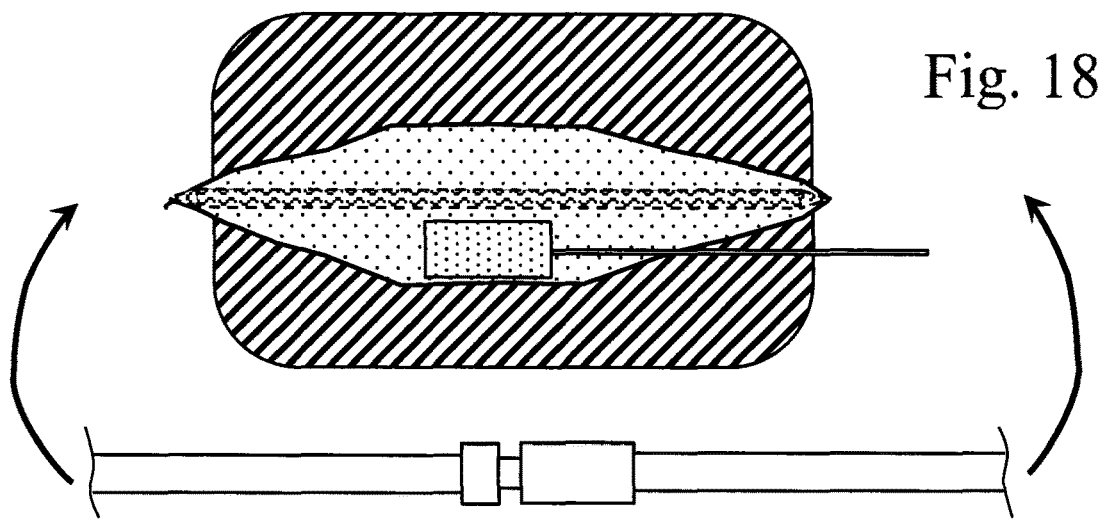
FIG. 18 is a plan view of the ninth embodiment in a second step of mounting.

Shortly before use, the protection sheet is removed from the lower portion 61 and the upper portion 64 is arranged along the weakening line 63 at the lower portion 61 as shown in FIG. 18. Thus, an area free from adhesive is formed in the middle of the adhesive lower portion 61.

The upper portion 64 may be shaped by the user into a desired shape, depending on the type of connector assembly to be monitored. If the connector assembly comprises a needle in one end, for example to the left in FIG. 19, the upper portion 64 is cut accordingly more narrow. The preparation may take place before actual use. If desired, the protective sheet may be applied again in order to protect the adhesive.

Finally, the connector assembly is arranged in place at the upper portion 64 and the lower adhesive portion 61 is folded up around the upper portion 64 at both sides and are attached to each other. The adhesive will stick only to the hose portions at the first and second ends of the closed pocket.

The above embodiments have different features which may be combined in different manners. Further modifications may occur to the skilled person.

In the claims, the term "comprises/comprising" does not exclude the presence of other elements or steps. Furthermore, although individually listed, a plurality of means, elements or method steps may be implemented by e.g. a single unit. Additionally, although individual features may be included in different claims or embodiments, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. Reference signs in the claims are provided merely as a clarifying example and shall not be construed as limiting the scope of the claims in any way.

Although the present invention has been described above with reference to specific embodiment and experiments, it is not intended to be limited to the specific form set forth herein. Rather, the invention is limited only by the accompanying claims and, other embodiments than those specified above are equally possible within the scope of these appended claims.

The invention claimed is:

1. A medical device for monitoring fluid leakage in a circuit enclosing said fluid, wherein the circuit comprises hoses and a connector and wherein the fluid is intended for communication with a patient, comprising
   a first sheet of a flexible material;
   a second sheet of a flexible material;
   an adhesive layer arranged at at least one of said first sheet and said second sheet in an arrangement for forming a closed pocket when the first sheet and the second sheet are brought together;
   said closed pocket having a first end and a second end constructed for receiving said hoses and an enlargement area there between constructed for receiving said connector;
   a detector device arranged for detecting leakage of said fluid intended for communication with the patient into the closed pocket;
   a tear-off strip, defined by a pair of weakening lines arranged in parallel with a mutual distance therebetween and extending across said first or second sheet and extending from said first end to said second end of said pocket;
   whereby the first sheet is attached to the second sheet via said adhesive layer to form said closed pocket for enclosing said hoses and connector to be monitored; and
   whereby when the device should be removed, the tear-off strip is ripped off, which effectively opens the closed pocket, so that the connector and hoses may be removed from the closed pocket.

2. The device according to claim 1, wherein said first sheet is connected to said tear-off strip by a first weakening line and said second sheet is connected to said tear-off strip by a second weakening line, whereby the first sheet, the tear-off strip and the second sheet form a single flexible sheet.

3. The device according to claim 1, wherein said adhesive is arranged with a distance to said tear-off strip.

4. The device according to claim 1, wherein said closed pocket is formed between said first sheet and said second sheet, and that at least one of said first or said second sheet is free from an adhesive layer in an area forming said closed pocket.

5. The device according to claim 1, wherein said detector device is an optical sensor arranged at said first or second sheet in a position to be included in said closed pocket when formed.

6. The device according to claim 1, wherein an indentation free from adhesive is formed in said adhesive portion for forming said enlargement area.

7. The device according to claim 1, further comprising a connector assembly, which is arranged along said tear-off strip for being enclosed in said pocket.

8. The device according to claim 5, wherein said optical sensor comprises:
an absorbent pad arranged at the middle of said tear-off strip or adjacent the middle of said tear-off strip and at said first portion comprising said adhesive; and
an optical fiber, having an internal end arranged in said absorbent pad and an external end extending out of the sheet.

9. A medical device for monitoring fluid leakage in a circuit enclosing said fluid, wherein the circuit comprises hoses and a connector and wherein the fluid is intended for communication with a patient, comprising
a first sheet of a flexible material;
a second sheet of a flexible material;
an adhesive layer arranged at at least one of said first sheet and said second sheet in an arrangement for forming a closed pocket when the first sheet and the second sheet are brought together;
a removable protection sheet covering said adhesive layer;
said closed pocket having a first end and a second end constructed for receiving said hoses and an enlargement area there between constructed for receiving said connector;
a detector device arranged for detecting leakage of said fluid intended for communication with the patient into the closed pocket;
a tear-off strip, defined by first and second lines arranged in parallel with a mutual distance across said first or second sheet, whereby said lines extend from said first end to said second end of said closed pocket;
whereby the first sheet is attached to the second sheet via said adhesive layer to form said closed pocket for enclosing said hoses and connector to be monitored so that the adhesive sticks to the hose and connector to a small extent;
and whereby when the device should be removed, the tear-off strip is ripped off, which effectively opens the closed pocket, so that the connector and hoses may be removed from the closed pocket.

10. The device according to claim 9, wherein said closed pocket has a size smaller than 20 ml.

11. The device according to claim 9, wherein said first sheet is connected to said tear-off strip by said first line and said second sheet is connected to said tear-off strip by said second line, whereby the first sheet, the tear-off strip and the second sheet form a single flexible sheet.

12. The device according to claim 9, wherein said closed pocket is formed between said first sheet and said second sheet, and that at least one of said first or second sheet is free from an adhesive layer in an area forming said closed pocket.

13. The device according to claim 9, further comprising a connector assembly arranged along said tear-off strip for being enclosed in said closed pocket.

14. The device according to claim 9, wherein said detector device is an optical sensor arranged at said first or second sheet in a position to be included in said closed pocket when formed.

15. The device according to claim 14, wherein said optical sensor comprises:
an absorbent pad arranged at the middle of said tear-off strip or adjacent the middle of said tear-off strip and at said first portion comprising said adhesive; and
an optical fiber, having an internal end arranged in said absorbent pad and an external end extending out of the sheet.

16. The device according to claim 9, wherein the tear-off strip is reinforced.

17. The device according to claim 9, wherein the tear-off strip is reinforced by additional material connected to the tear-off strip.

18. The device according to claim 9, wherein the tear-off strip is reinforced by being made in a stiff plastic material forming a reinforcement.

19. The device according to claim 9, wherein the tear-off strip is arranged at a portion of the first sheet or second sheet, which does not comprise an adhesive.

20. The device according to claim 9, wherein the tear-off strip comprises a grip portion arranged at one or both ends of the tear-off strip.

21. A medical device for monitoring fluid leakage in a circuit enclosing said fluid, wherein the circuit comprises hoses and a connector and wherein the fluid is intended for communication with a patient, comprising
a first sheet of a flexible material;
a second sheet of a flexible material;
an adhesive layer arranged at said first sheet or said second sheet or both in an arrangement for forming a closed pocket when the first sheet and the second sheet are brought together;
a removable protection sheet covering said adhesive layer before us;
said closed pocket having a first end and a second end constructed for receiving said hoses and an enlargement area there between constructed for receiving said connector;
a detector device arranged for detecting leakage of said fluid intended for communication with the patient into the closed pocket;
said detector device being an optical sensor arranged at said first or second sheet in a position to be included in said closed pocket when formed;
a tear-off strip, defined by first and second lines arranged in parallel with a mutual distance across said first or second sheet, whereby said lines extend from said first end to said second end of said closed pocket and whereby the tear-off strip is constructed by the first sheet or second sheet so that the tear-off strip connects the first sheet and the second sheet;
wherein the tear-off strip is reinforced and is arranged at a portion of the first sheet or second sheet, which does not comprise an adhesive;
whereby the first sheet is folded to be attached to the second sheet via said adhesive layer to form said closed pocket for enclosing said hoses and connector to be monitored so that the adhesive sticks to the hose and connector to a small extent; and
whereby when the device should be removed, the tear-off strip is ripped off, which effectively opens the closed pocket, so that the connector and hoses may be removed from the closed pocket.

* * * * *